United States Patent
Tegels et al.

(10) Patent No.: US 9,370,345 B2
(45) Date of Patent: Jun. 21, 2016

(54) BIOADHESIVE DELIVERY CATHETER MANIFOLD WITH MIXING FIXTURE AND METHODS

(71) Applicant: St. Jude Medical Puerto Rico LLC, Caguas, PR (US)

(72) Inventors: Zachary J. Tegels, Minneapolis, MN (US); Robert M. Vidlund, Forest Lake, MN (US); Doreen Borgmann, Hopkins, MN (US); Edward E. Parsonage, St. Paul, MN (US); Martha Escobar, Jordan, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 441 days.

(21) Appl. No.: 13/744,018

(22) Filed: Jan. 17, 2013

(65) Prior Publication Data

US 2013/0190808 A1    Jul. 25, 2013

Related U.S. Application Data

(60) Provisional application No. 61/589,930, filed on Jan. 24, 2012.

(51) Int. Cl.
*A61B 17/00* (2006.01)
(52) U.S. Cl.
CPC ... *A61B 17/00491* (2013.01); *A61B 2017/0065* (2013.01); *Y10T 29/49826* (2015.01)
(58) Field of Classification Search
CPC .............. A61B 17/00491; A61B 2017/00495; A61B 2017/0065; A61M 5/178
See application file for complete search history.

(56) References Cited

U.S. PATENT DOCUMENTS

| | | |
|---|---|---|
| 8,333,787 B2 | 12/2012 | Pipenhagen et al. |
| 8,506,592 B2 | 8/2013 | Killion et al. |
| 2010/0217231 A1 | 8/2010 | Ilan et al. |
| 2011/0166595 A1 | 7/2011 | Vidlund et al. |
| 2011/0282383 A1 | 11/2011 | Vidlund et al. |
| 2013/0006299 A1 | 1/2013 | Pipenhagen et al. |

FOREIGN PATENT DOCUMENTS

| | | |
|---|---|---|
| EP | 0716833 A2 | 6/1996 |
| WO | 9633658 A1 | 10/1996 |
| WO | 9807372 A2 | 2/1998 |
| WO | 2006074044 A2 | 7/2006 |

OTHER PUBLICATIONS

Notification of Transmittal of the International Search Report and the Written Opinion of the International Searching Authority, or the Declaration for International Application No. PCT/US2013/021800, mailed Apr. 12, 2013 (15 pp.).
Tegels et al., U.S. Appl. No. 61/590,000, filed Jan. 24, 2012.

*Primary Examiner* — Ashley Fishback
(74) *Attorney, Agent, or Firm* — Holland & Hart (57) ABSTRACT

A bioadhesive delivery catheter includes a manifold, a dual lumen tube, and a mixing member. The manifold includes a delivery device passage and an injection port. The tube is insertable into the delivery device passage and includes first and second lumens positioned side-by-side. The first lumen extends proximal of the second lumen within the delivery device passage, and the second lumen is in flow communication with the injection port. The mixing member is positioned between a proximal inlet of the injection port and the second lumen and is configured to help mix a bioadhesive material that is delivered through the injection port into the second lumen.

20 Claims, 8 Drawing Sheets

BIOADHESIVE DELIVERY CATHETER MANIFOLD WITH MIXING FIXTURE AND METHODS

CROSS-REFERENCE TO RELATED APPLICATION

This application claims the benefit of the filing date of U.S. Provisional Application No. 61/589,930, filed Jan. 24, 2012, and entitled BIOADHESIVE DELIVERY CATHETER MANIFOLD WITH MIXING FIXTURE AND METHODS, the disclosure of which is incorporated, in its entirety, by this reference.

TECHNICAL FIELD

The present disclosure relates generally to a method and system for handling bioadhesive materials, and more particularly, to methods and systems for storing, mixing and dispensing bioadhesive material for use in sealing tissue punctures.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one primary problem is ensuring a complete seal of the puncture. One technique includes the use of a bioadhesive material to seal the puncture. Some types of bioadhesive materials must be activated prior to use, and should be activated just prior to use in order to avoid premature activation of the bioadhesive material that would affect its performance. The handling and activation of bioadhesive materials in the context of vascular and other tissue puncture closure devices present a number of challenges.

SUMMARY

One aspect of the present disclosure relates to a bioadhesive delivery catheter that includes a manifold, a dual lumen tube, and a mixing member. The manifold includes a delivery device passage and an injection port. The tube is insertable into the delivery device passage and includes first and second lumens positioned side-by-side. The first lumen extends proximal of the second lumen within the delivery device passage, and the second lumen is in flow communication with the injection port. The mixing member is positioned between a proximal inlet of the injection port and the second lumen.

A proximal end of the tube may include a taper. The tube may have a reduced profile at a proximal end at a location proximal of the second lumen. The mixing member may include a mixing chamber defined within the delivery device passage adjacent to the tube. The mixing member may include a mixing insert positioned within the injection port. The mixing member may include at least first and second mixing inserts positioned in a passage defined in the manifold between the injection port and the delivery device passage.

The manifold may include a bioadhesive passage that extends from the injection port to the delivery device passage, and the mixing member may be positioned in the bioadhesive passage. The delivery device passage may include proximal and distal passage portions, wherein the proximal passage portion has a smaller cross-sectional shape than the distal passage portion. The injection port may define a bioadhesive passage that intersects with the distal passage portion.

Another aspect of the present disclosure relates to a method of delivering a bioadhesive material that includes providing a delivery device, a manifold, and a tube, wherein the manifold includes a delivery device passage and an injection port, and the tube includes first and second lumens positioned side-by-side. The first lumen extends proximal of the second lumen, and the tube is insertable into the delivery device passage with the second lumen in flow communication with the injection port. The method also includes extending the delivery device through the first lumen and into a vessel puncture to locate the vessel puncture, and delivering the bioadhesive material through the injection port and the second lumen to the vessel puncture to seal closed the vessel puncture.

The method may further include mixing the bioadhesive material while delivering the bioadhesive material through the manifold. The tube may include a reduced profile at a proximal end of the tube. The manifold may include a mixing chamber positioned proximal of a proximal opening into the second lumen, and the method includes mixing the bioadhesive material in the mixing chamber during delivery of the bioadhesive material into the second lumen. The mixing member may be positioned in the injection port, and the method includes mixing the bioadhesive material with the mixing member during delivery of the bioadhesive material into the second lumen.

A further aspect of the present disclosure relates to a method of forming a bioadhesive delivery catheter. The method includes forming a manifold having a delivery device passage and an injection port, forming a tube having first and second lumens, the first lumen extending further proximally than the second lumen, inserting the tube into the delivery device passage to provide flow communication between the second lumen and the injection port, and positioning a sealant mixing member between an inlet to the injection port and an opening into the second lumen.

The sealant mixing member may include a protrusion that creates turbulence in a flow of bioadhesive material delivered into the injection port. The sealant mixing member may include a mixing chamber that is in fluid communication with the delivery device passage. The delivery device passage may include proximal and distal passage portions having different cross-sectional sizes, and the tube may have a reduced cross-section proximal end portion sized for insertion into the proximal passage portion. The method may include forming a taper in a proximal end portion of the tube that overlaps with a proximal opening into the second lumen of the tube. The method may include bonding the tithe to the manifold within the delivery device passage.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

Throughout the drawings, identical reference numbers designate similar, but not necessarily identical, elements.

DETAILED DESCRIPTION

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in this specification and the appended claims, the terms "engage" and "engagable" are used broadly to mean interlock, mesh, or contact between two structures or devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising." The terms "biomaterial" or "composition" refer to a material intended to interface with biological systems to preferably evaluate, treat, or seal any tissue, organ or function of the body. Biomaterial refers to the complete material (precursor molecules plus all additives, base or solvents and bioactive agents, if any) at and after having reached and passed its gel-point. Composition refers to the complete material before having reached its gel-point. The term "gel" refers to the state of matter between liquid and solid. As such, a gel has some of the properties of a liquid (i.e., the shape is resilient and deformable) and some of the properties of a solid (i.e., the shape is discrete enough to maintain three dimensions on a two dimensional surface).

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

An exemplary embodiment of the present disclosure relates to a vascular closure device configured to deliver a volume of bioadhesive material to a vessel punctured to seal close the vessel puncture. The vascular closure device includes a manifold and a dual lumen tube connected to the manifold. The manifold includes a base portion that defines a delivery device passage, and an injection port that defines a bioadhesive passage. One lumen of the dual lumen delivery tube is connected in flow communication with an inlet to the delivery device passage. The other lumen of the dual lumen delivery tube is connected in flow communication with the bioadhesive passage of the injection port. The first lumen may extend further proximally than the second lumen. The manifold may further define a mixing chamber or other mixing feature that provides at least some mixing of the bioadhesive material prior to entering into the second lumen and being delivered to the vessel puncture. The bioadhesive material may include a biomaterial. The bioadhesive material may include multiple components (e.g., compositions) that require mixing prior to delivery to the tissue puncture.

An opposite or distal end of the delivery tube includes a balloon mounted thereto that is arranged in flow communication with the first lumen. The second lumen terminates at a distal opening that is positioned proximal of the balloon. In operation, the balloon is positioned within the vessel and inflated to temporarily seal closed the vessel puncture from within the vessel. The bioadhesive material is then delivered through the second lumen to a location outside of and adjacent to the vessel to seal closed the vessel puncture from outside of the vessel. Thereafter, the delivery tube is removed through the bioadhesive material that has been deposited outside of the vessel.

The vascular closure device may include a balloon locating device used to deliver a secondary flow of bioadhesive material that seals closed a passage left in the first volume of bioadhesive material upon removal of the delivery tube. The balloon locating device may also, or alternatively, deposit a detachable sealing tip within the first volume of bioadhesive material to seal closed a passage in the first volume of bioadhesive material left upon removal of the delivery tube. The balloon locating device may provide a manifold for delivery of inflation fluid into the first lumen and to the balloon.

One example bioadhesive delivery manifold in accordance with the present disclosure includes a mixing member in place of or in addition to the mixing chamber. The mixing member may be positioned, for example, at the injection port, within the bioadhesive passage, or within the mixing chamber. The mixing member may be in the form of, for example, a fin, a corkscrew member, a plurality of threads, a baffle, or other structure that induces turbulence in or disrupts the flow path of the bioadhesive material being delivered to the second lumen of the delivery tube.

Referring now to FIGS. 1A-5B, an example vascular closure device 10 is shown and described. The vascular closure device 10 includes a manifold 12, a delivery tube 14, and a balloon location device 16. The delivery tube 14 is inserted into one end of the manifold 12. A portion of the balloon location device 16 is inserted into an opposite end of the manifold 12 and through one of the lumens of the delivery tube 14. The delivery tube 14 includes at least two separate and distinct lumens that are positioned side-by-side. One of the lumens is used to deliver inflation fluid to a balloon that is positioned at a distal end of the delivery tube 14. The other lumen is used for delivery of a bioadhesive material from the manifold 12 to a distal end of the delivery tube 14 at a location proximal of the balloon. The manifold 12 is configured to provide at least some mixing of the bioadhesive material prior to and during delivery of the bioadhesive material into the delivery tube 14.

Figures 1A, 1B, 1C:
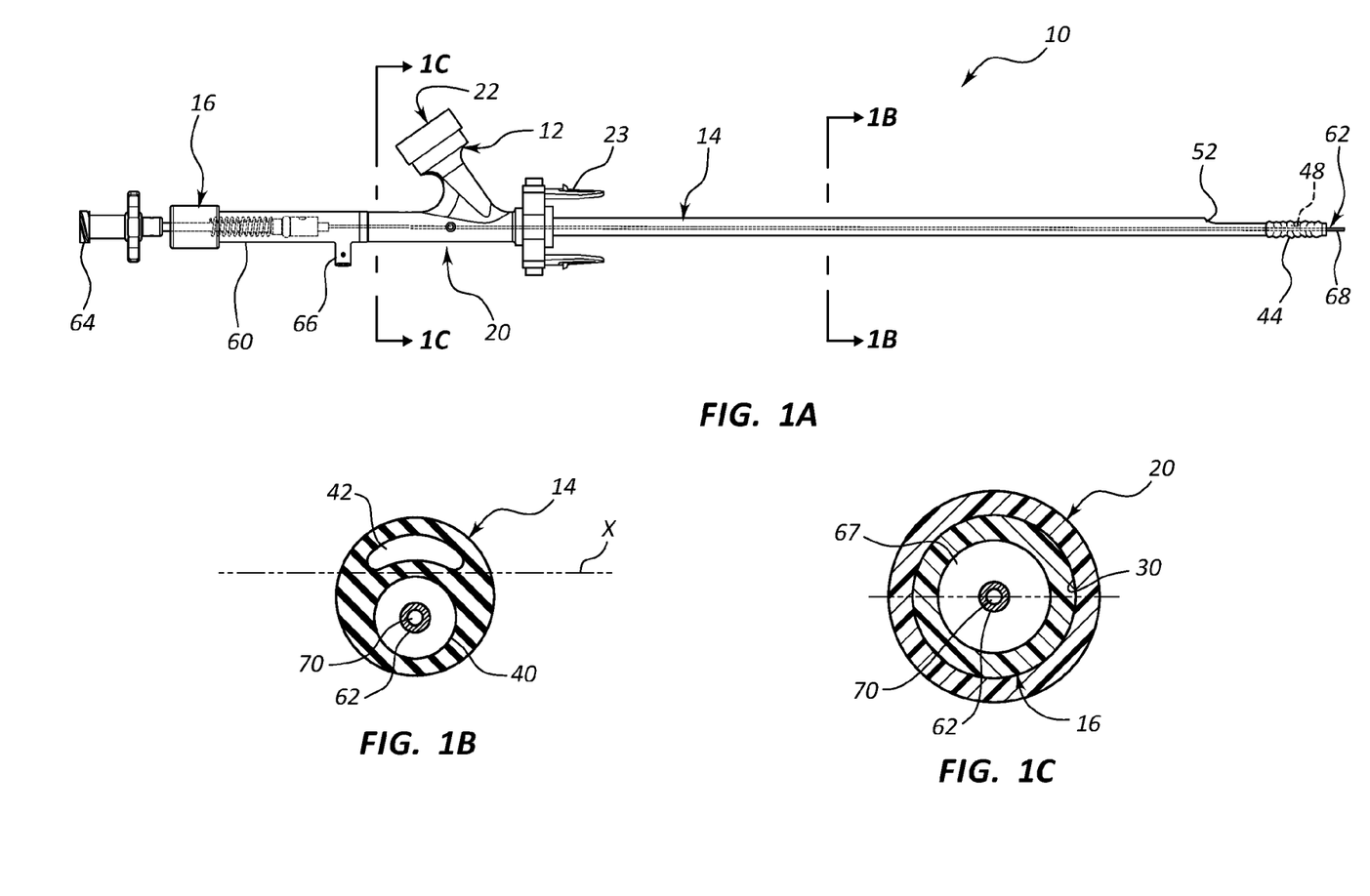
FIG. 1A is a side view of an example vascular closure device in accordance with the present disclosure.
FIG. 1B is a cross-sectional view of the vascular closure device of FIG. 1A taken along cross-section indicators 1B-1B.
FIG. 1C is a cross-sectional view of the vascular closure device of FIG. 1 taken along cross-section indicators 1C-1C.
Figure 2:
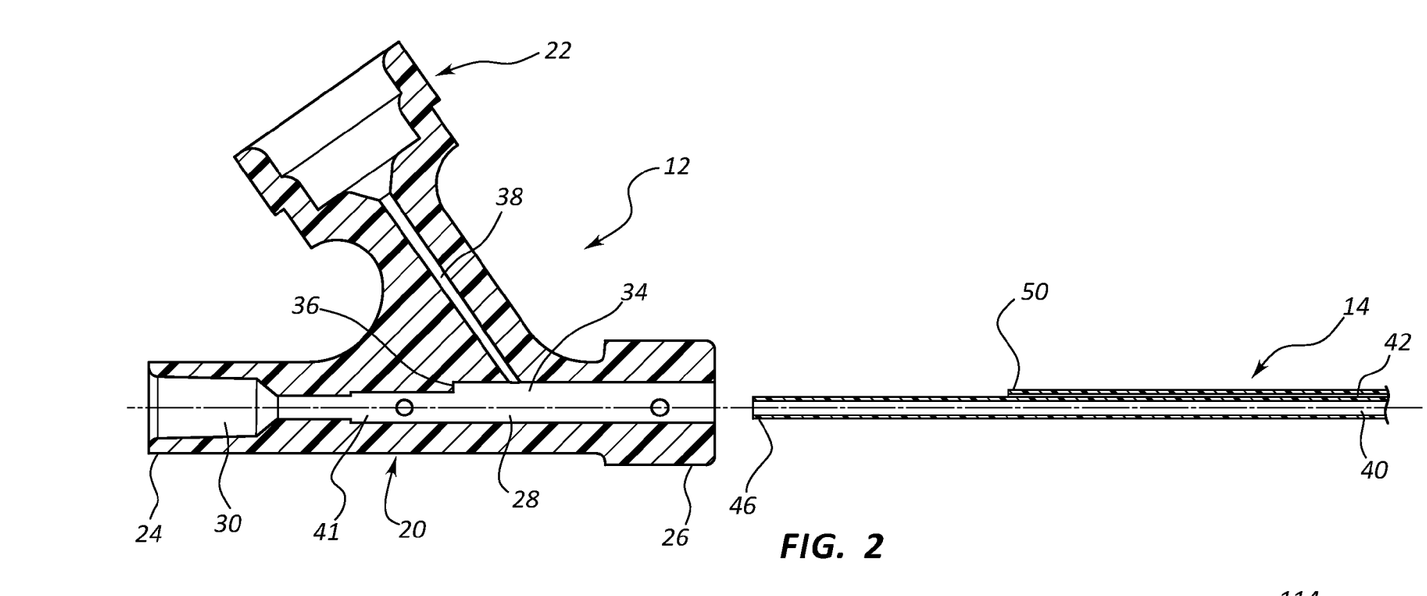
FIG. 2 is a cross-sectional side view of a manifold and a portion of a delivery tube of the vascular closure device of FIG. 1.

The manifold 12 includes a base 20, an injection port 22, and a latch 23 (see FIGS. 1A and 2). The base 20 includes proximal and distal ends 24, 26, a delivery device passage 28 and a proximal seat 30 in communication with the delivery device passage 28, a distal opening 32, also in flow communication with delivery device passage 28, a mixing chamber 34, and a step 36 defined within the delivery device passage 28. The delivery device passage 28 is sized to receive a proximal end of the delivery tube 14. The proximal seat 30 is sized to receive a portion of the balloon location device 16. The step 36 is positioned at a location along a length of the delivery device passage 28 that is distal of the proximal seat 30 and proximal of a bioadhesive passage 38 of the injection port 22 (see FIG. 2). The mixing chamber 34 is typically defined at least partially within the delivery device passage 28. The mixing chamber 34 may be arranged adjacent to the bioadhesive passage 38. The mixing chamber 34 may include an open space or cavity within which the bioadhesive material may mix and flow after being expelled from the bioadhesive passage 38 and prior to entry into the delivery tube 14.

Figure 3:
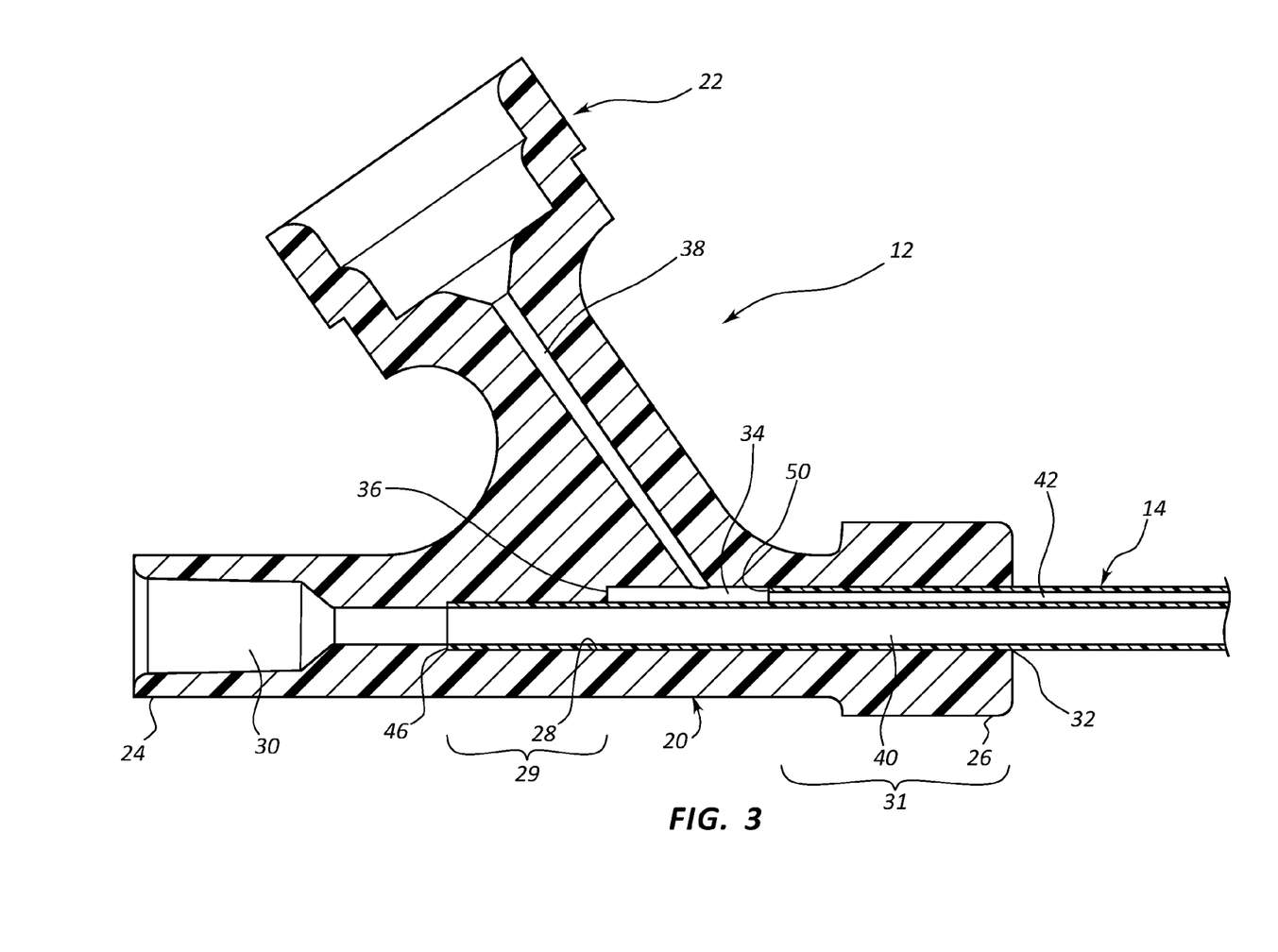
FIG. 3 is a cross-sectional side view of the manifold and delivery tube of FIG. 2 assembled together.
Figure 5A:
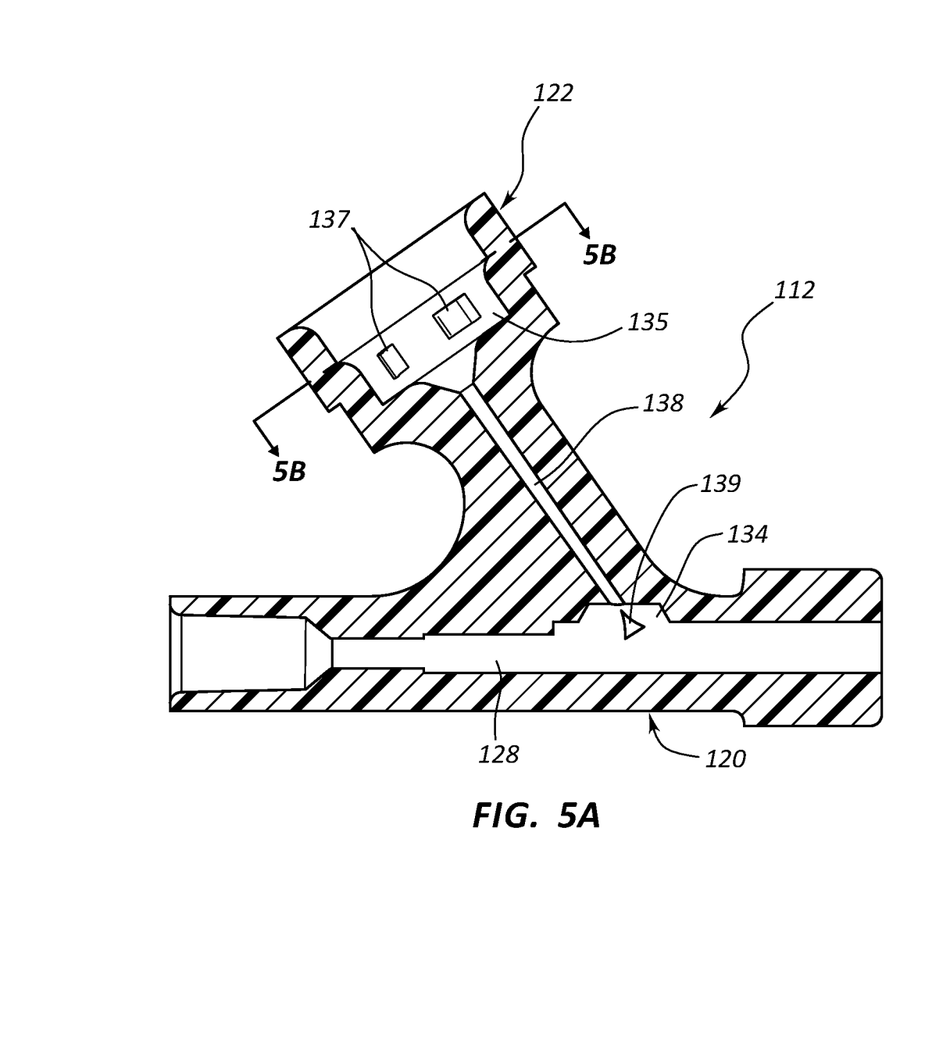
FIG. 5A is a cross-sectional side view of another example manifold in accordance with the present disclosure.

FIG. 3 shows one configuration for the mixing chamber 34. FIG. 5A shows another mixing chamber 134 embodiment having a different shape and size. The mixing chamber 134 may have an increased size as compared to mixing chamber 34, which may provide additional space for mixing of the bioadhesive material prior to entering the delivery tube 14.

The latch 23 may be used to connect the manifold 12 to an insertion sheath such as the sheath 2 shown in FIGS. 6-9. The latch 23 may include at least one latch member that connects to a hub 4 of the sheath 2, thereby limiting at least some axial movement of the manifold 12 relative to the sheath 2. In other arrangements, the manifold 12 may be operable without the latch 23 and be able to move independent of the sheath 2 during operation of the vascular closure device 10.

The delivery tube 14 may be a dual lumen tube that includes at least first and second lumens 40, 42. The delivery tube 14 may be formed using an extrusion process. The first lumen 40 includes proximal and distal openings 46, 48 (see FIGS. 1A and 2). The proximal opening 46 is in flow communication with the proximal seat 30 of the manifold 12. The distal opening 48 is open to an interior of a balloon 44 that is positioned at a proximal end of the delivery tube 14 (see FIG. 1A).

The second lumen 42 includes proximal and distal openings 50, 52. The proximal opening 50 is in flow communication with the mixing chamber 34. The distal opening 52 is open at a distal end portion of the delivery tube 14 that is located proximal of the balloon 44. Typically, the first lumen 40 is configured to deliver an inflation fluid delivered through the balloon location device 16 and to the balloon 44. The second lumen 42 is typically configured to deliver a flow of bioadhesive material from the injection port 22, through the bioadhesive passage 38, and through the mixing chamber 34 and second lumen 42 to the distal opening 52. Typically, the distal opening 52 is positioned proximal of the balloon 44 and located outside of a vessel puncture that is to be treated as described below with reference to FIGS. 6-9.

The first and second lumens 40, 42 are positioned side-by-side. The first lumen 40 may have, for example, a generally circular cross-sectional shape (see FIG. 1B). The second lumen 42 may have, for example, a generally crescent cross-sectional shape as (see FIG. 1B). Other configurations are possible, including one in which the first and second lumens 40, 42 each have a generally circular cross-sectional shape. Providing at least one of the first and second lumens 40, 42 with a crescent or oval cross-sectional shape may help reduce an outer profile of the delivery tube 14. Reducing the outer profile of the delivery tube 14 may help reduce an outer profile of the manifold 12 and help limit damage to a tissue puncture through which the delivery tube 14 is advanced for treatment purposes.

Figure 4:
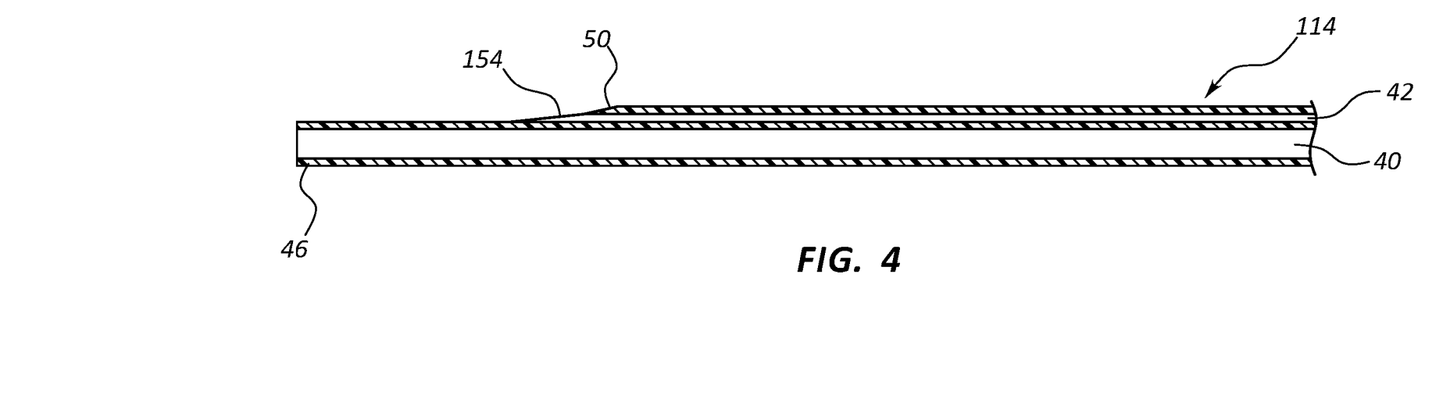
FIG. 4 is a cross-sectional view of a proximal end portion of another example delivery tube in accordance with the present disclosure.

The delivery tube 14 may be tapered at its distal end. In one example, the delivery tube 14 is tapered from the proximal opening 50 of the second lumen 42 towards the proximal opening 46 of the first lumen 40. FIG. 4 shows an alternative delivery tube 114 that includes a tapered surface 154. The tapered surface 154 may be formed using, for example, skiving, laser cutting, or drilling. The tapered surface 154 may be formed along portions of the proximal end portion of the delivery tube 14. The tapered surface 154 may improve insertability of the delivery tube 14 into the manifold 12 and provide an improved flow of the bioadhesive material into the second lumen 42. The tapered surface 154 may be maintained outside of the first lumen 40, such as vertically above a separation plane X as shown in FIG. 1B.

The balloon location device 16 may include a housing 60, an inner tube 62, an inner tube manifold 64, an inflation fluid manifold 66, and an inflation lumen 67 (see FIGS. 1A and 1C). The balloon location device 16 may provide inflation fluid to the first lumen 40 of the delivery tube 14 through the inflation fluid manifold 66 and inflation lumen 67 (see FIGS. 1A and 1C). The inflation fluid may flow around the inner tube 62 within the housing 60, manifold 12, and delivery tube 14. The inflation fluid may flow to the balloon 44 for inflating the balloon 44 when the balloon 44 is positioned extending through a vessel puncture and within a vessel lumen. The balloon may be deflated by applying a vacuum pressure to withdraw the inflation fluid out of the balloon 44 and through the inflation fluid manifold 66.

Figure 9:
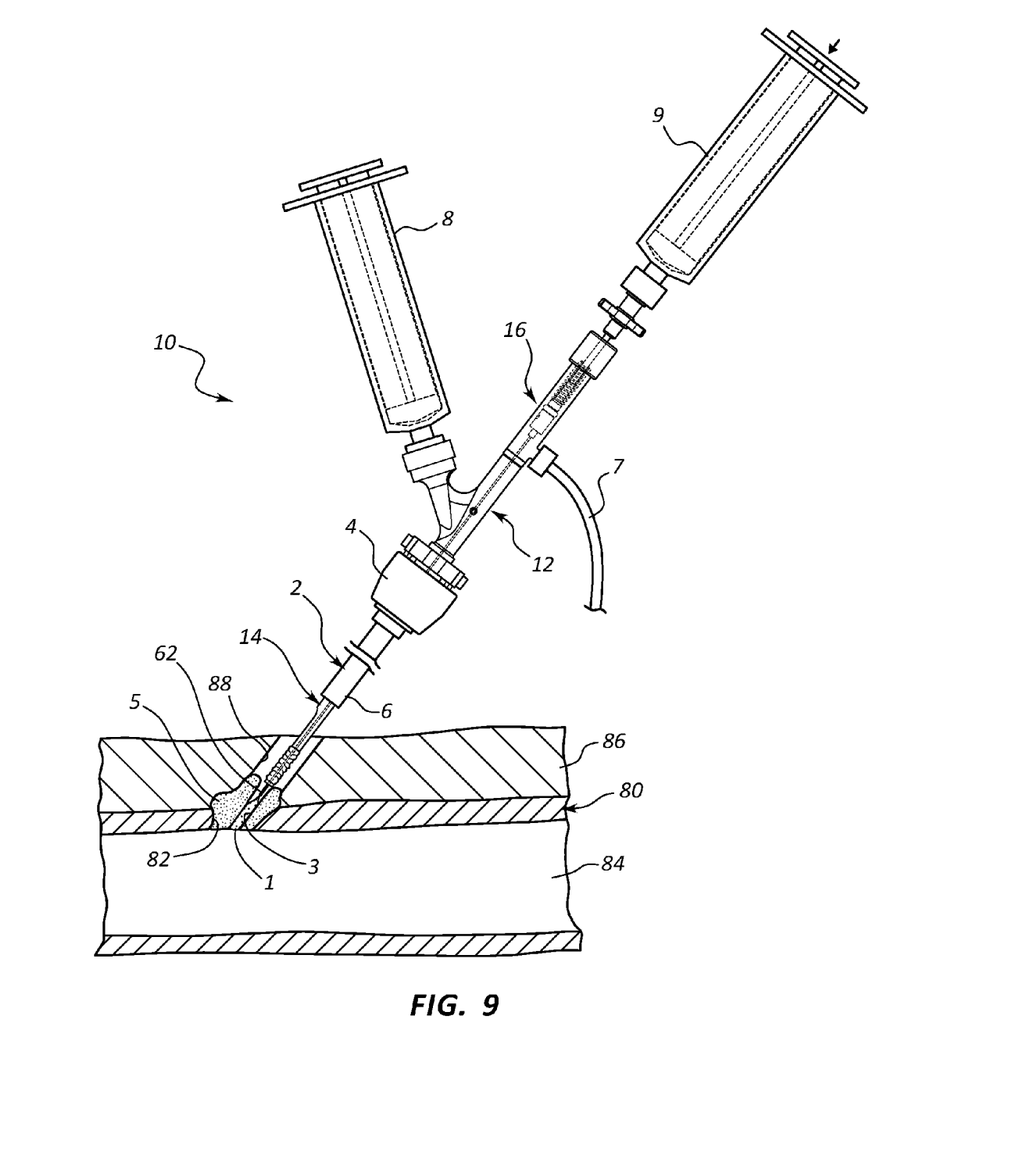

The inner tube 62 may extend through the housing 60, the delivery device passage 28, and out of the distal opening 48 of the first lumen 40 to a position distal of the delivery tube 14. The inner tube 62 may have a variety of purposes, including, for example, delivery of a secondary bioadhesive material and providing a pathway for a suture (not shown) to the distal end of the balloon location device 16. FIG. 9 illustrates delivery of the secondary bioadhesive material within a deposited first bioadhesive material after removal of the delivery tube 14 through the deposited first bioadhesive material. More details concerning operation of the inner tube 62 are described below with reference to FIG. 9.

The inner tube 62 may include a distal end 68 and an inner tube lumen (see FIGS. 1A and 1C). A distal end of the balloon 44 may be secured to the inner tube 62. Inflating the balloon 44 may move the inner tube 62 relative to the housing 60, thereby visually showing an inflation condition of the balloon 44. More details concerning operation of a balloon location device for purposes of, for example, showing an inflation condition of an inflation balloon are described with reference to U.S. Patent Application No. 61/590,000 filed on 24 Jan. 2012 and entitled "Balloon Location Device Manifold for Vascular Closure Device and Methods," which application is incorporated herein in its entirety by this reference.

The inner tube manifold 64 may be configured to be attached to a secondary bioadhesive carrier 9 as described below with reference to FIG. 9. In other arrangements, the inner tube manifold 64 may be used to connect other devices and provide delivery of different types of fluids to the inner tube 62.

Referring again to FIGS. 2 and 3, the delivery tube 14 may be secured within the manifold 12 using an adhesive or other bonding agent in a proximal passage portion 29 of the delivery device passage 28 (see FIG. 3). The bond formed by the adhesive may secure the delivery tube 14 to the manifold 12 and provide a seal that limits passage of the bioadhesive material within the mixing chamber 34 from advancing distally into the proximal seat 30.

The delivery tube 14 may be secured to a proximal passage portion 41 of the delivery device passage 28 using, for example, an adhesive or other bonding agent, an interference fit, or other connection provided between the delivery tube 14 and the distal passage portion 31. The connection between the delivery tube 14 and distal passage portion 31 may limit passage of the bioadhesive material from the mixing chamber 34 distally out of the distal opening 32 in the manifold 12.

In other arrangements, the bioadhesive material, when delivered into the delivery device passage 28, may be used to provide, at least in part, a seal between the delivery tube 14 and the manifold 12.

In some arrangements, the delivery tube 14 may include a strain relief feature where the delivery tube 14 extends out of the distal opening 32 of the manifold 12. The strain relief feature may include, for example, a coil structure or other feature that resists crimping or crushing of the delivery tube 14.

Figure 5B:
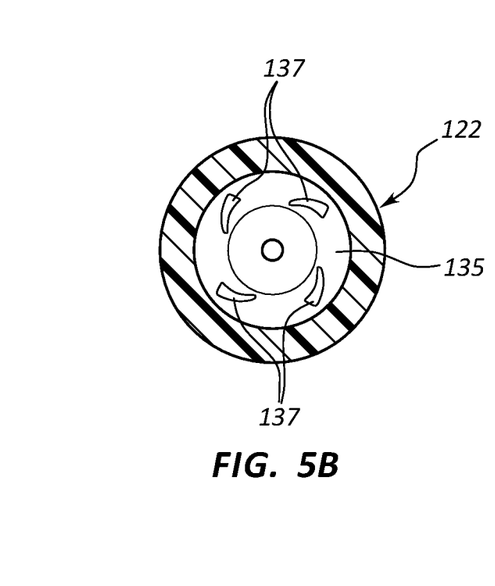
FIG. 5B is a cross-sectional view of the manifold of FIG. 5A taken along cross-section indicators 5B-5B.

Referring now to FIGS. 5A and 5B, an alternative manifold 112 is shown including a base 120 and an injection port 122. The base 120 includes a delivery device passage 128, a mixing chamber 134, and a preliminary mixing chamber 135. The injection port 122 includes a bioadhesive passage 138. The preliminary mixing chamber 135 may be positioned proximal of the bioadhesive passage 138. The mixing chamber 134 may be positioned distal of the bioadhesive passage 138. The mixing chamber 134 and preliminary mixing chamber 135 may be configured to provide at least some mixing of a bioadhesive material prior to delivering the bioadhesive material to the second lumen 42 of the delivery tube 14.

The manifold 112 may also include a set of first mixing members 137 positioned within the preliminary mixing chamber 135. At least one second mixing member 139 may be positioned within the mixing chamber 134. The first and second mixing members 137, 139 may have any desired shape and size, and be arranged in any desired configuration. FIG. 5B shows the first mixing members 137 each having a contoured shape and being arranged in a spiral pattern. The second mixing member 139 is shown having a generally wedge-shaped construction. Many other shapes, sizes and arrangements are possible for the first and second mixing members 137, 139. The first and second mixing members 137, 139 may be arranged and configured to provide at least some agitation and turbulence in the flow of bioadhesive material to improve mixing and activation of the bioadhesive material prior to entry into the second lumen 42. The first and second mixing members 137, 139 may be mounted to the manifold 112 using a releasable connection, or may be integrally formed as a single piece with the manifold.

In other arrangements, the bioadhesive passage 138 may be configured with a shape or other feature that provides enhanced mixing of the bioadhesive material. In one example, the bioadhesive passage 138 includes a corkscrew configuration. In another embodiment, the bioadhesive passage 138 includes a helical shaped thread or rib.

Figure 6:
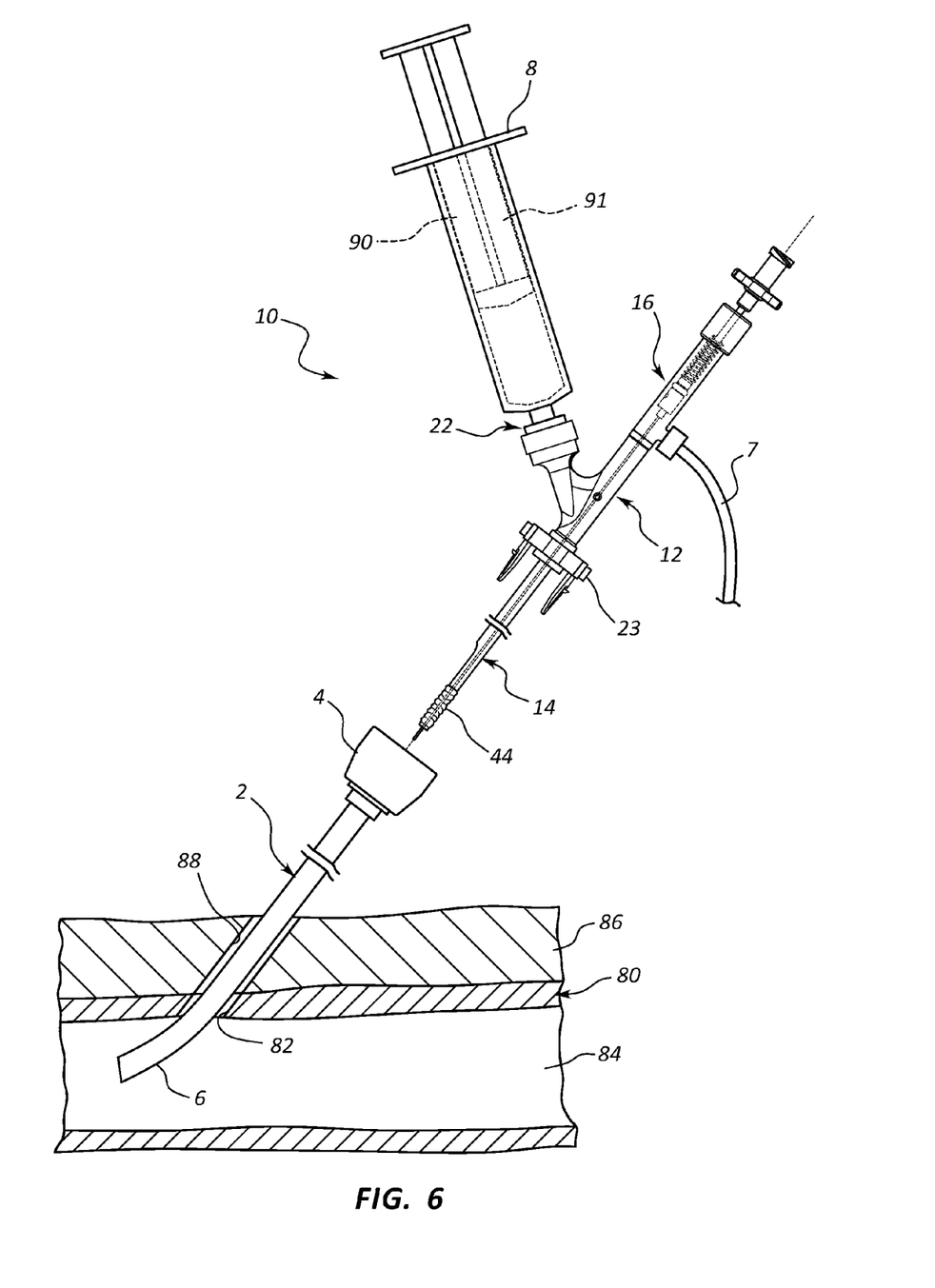
FIGS. 6-9 show example steps of operating the vascular closure device of FIG. 1 as part of a procedure to seal a vessel puncture.
Figure 7:
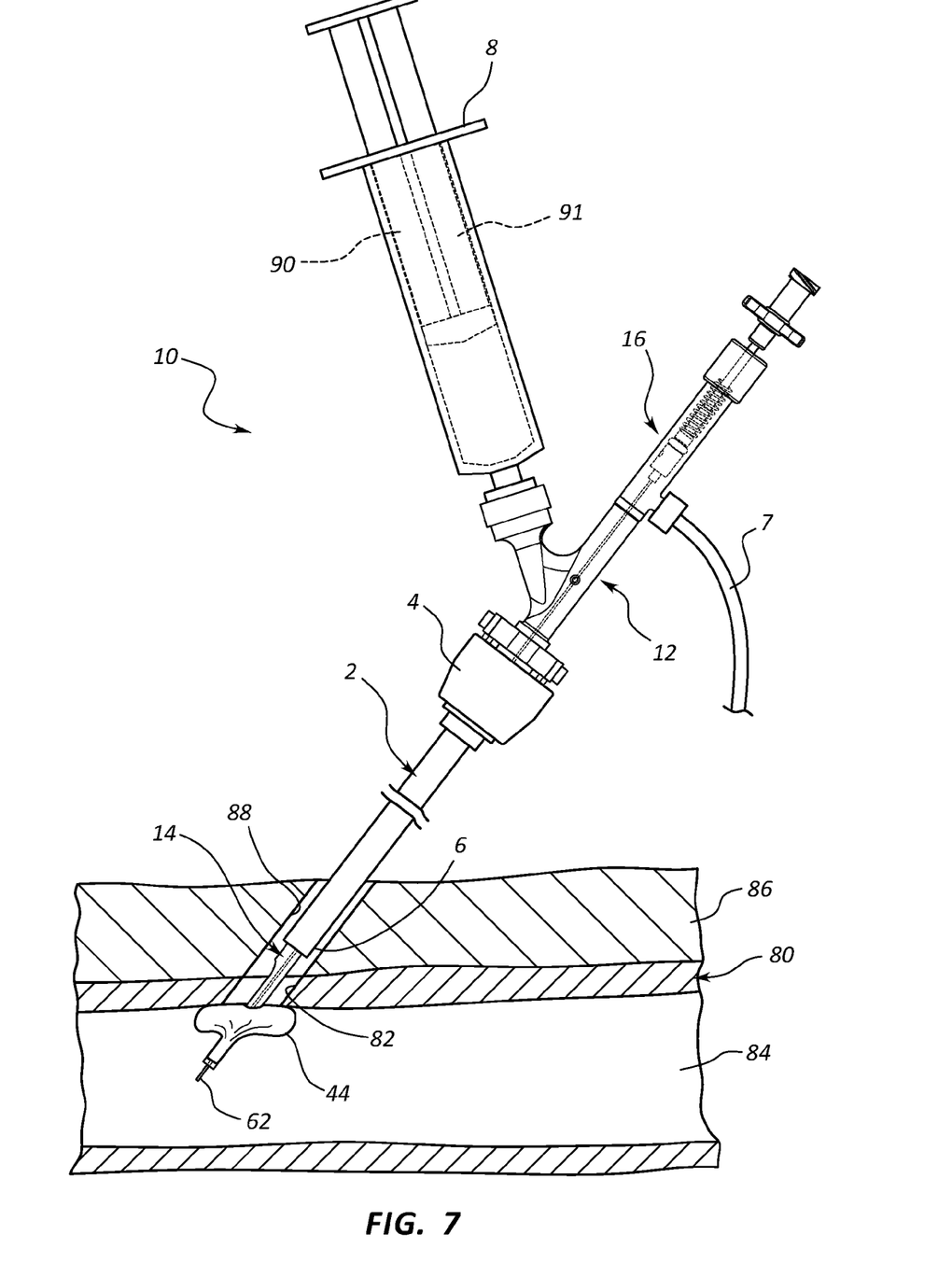

Referring now to FIGS. 6-9, an example method of treating a vessel puncture is shown and described. FIG. 6 illustrates a sheath 2 having a distal end 6 thereof advanced through a vessel puncture 82 of a vessel 80 and into the vessel lumen 84. The sheath 2 extends through a tissue tract 88 of a tissue layer 86 prior to advancing through the vessel puncture 82. A distal end of the vascular closure device 10 is inserted into the hub 4 of the sheath 2 until the latch 23 of the manifold 12 engages with the hub 4 as shown in FIG. 7. The balloon 44 is inflated by delivering a volume of inflation fluid from an inflation fluid source 7, through the balloon location device 16 and manifold 12 and into the first lumen 40 of the delivery tube 14. The vascular closure device 10 and sheath 2 are retracted together until the inflated balloon 44 contacts an inner surface of the vessel 80 to temporarily seal closed the vessel puncture 82.

A bioadhesive material is delivered from a first bioadhesive carrier 8, through the injection port 22 of the manifold 12, and into the second lumen 42. The first and second bioadhesive carriers 8, 9 may include chambers 90, 91 (see FIG. 6) that each hold a component of the first bioadhesive material. The components held in the chambers 90, 91 may be mixed together as the first bioadhesive material is delivered into and through the manifold 12 before entering the second lumen 42. Mixing the components may activate the components. The first and second bioadhesive carriers 8, 9 may be constructed as a syringe, such as disclosed in U.S. patent application Ser. No. 13/106,707 filed on 12 May 2011 and entitled "Bioadhesive Applicator and Methods of Sealing Tissue Punctures Using Same," which application is incorporated herein in its entirety by this reference.

Figure 8:
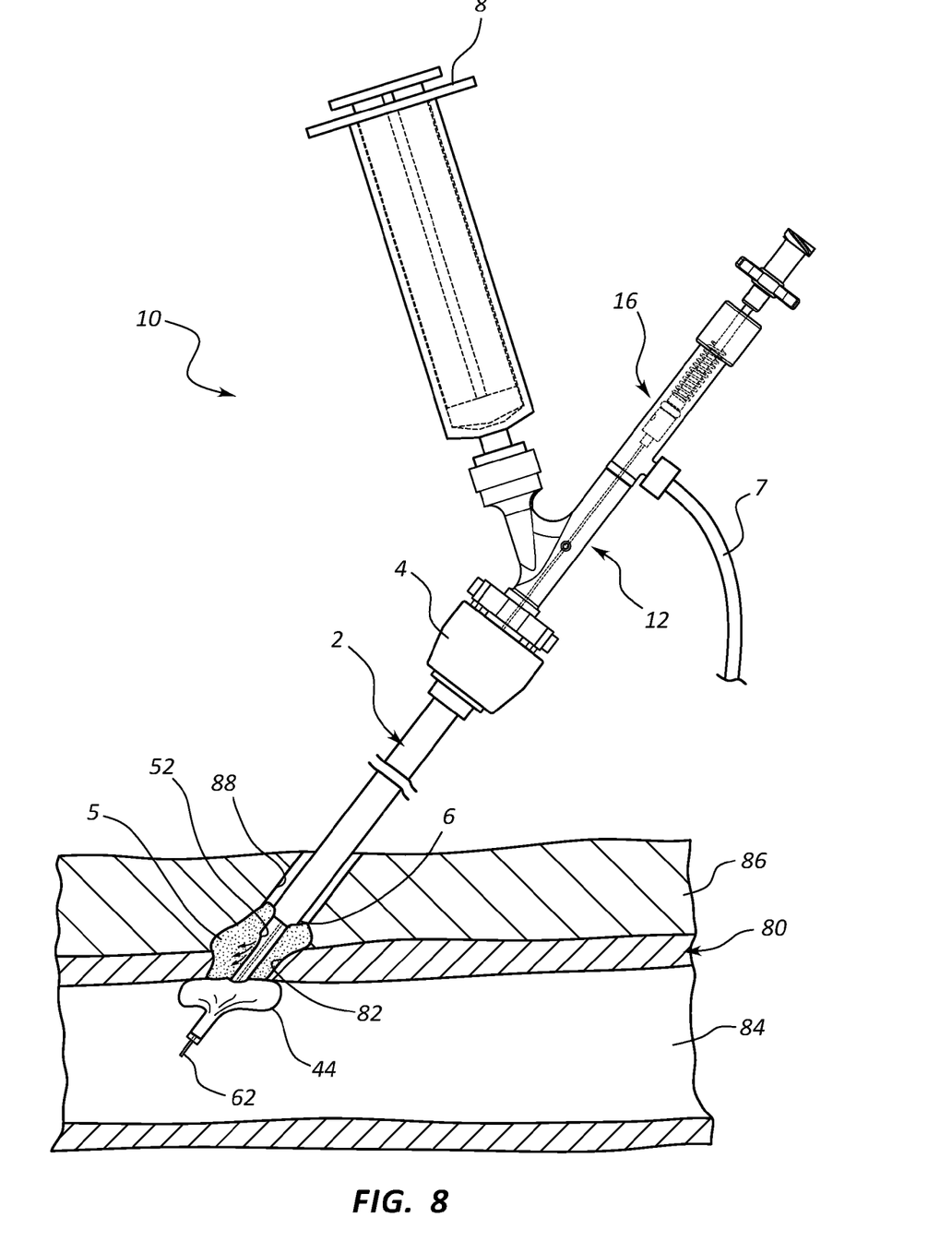

The bioadhesive material is expelled out through the distal opening 52 to a location within the tissue tract 88 adjacent to the vessel puncture 82, as shown in FIG. 8. The bioadhesive material may form a bioadhesive plug 5. The bioadhesive material may flow to at least partially fill the vessel puncture 82 and tissue tract 88 and a space between the vessel 80 and tissue layer 86. The bioadhesive material may be allowed to cure for a predetermined amount of time to at least partially solidify and maintain a shape as the bioadhesive plug 5.

Once the bioadhesive material is at least partially cured into the bioadhesive plug 5, the balloon 44 is deflated via the inflation fluid source 7, and the delivery tube 14 is withdrawn through the bioadhesive plug 5, as shown in FIG. 9. Removing the delivery tube 14 through the bioadhesive plug 5 may leave a tract 3 through the bioadhesive plug 5. The tract 3 may be at least partially filled or plugged by delivering a second bioadhesive material from the second bioadhesive carrier 9, through the inner tube 62 and out of the distal end 68 of the inner tube 62, as shown in FIG. 9. The second bioadhesive material may form a secondary bioadhesive plug 1 that seals closed the tract 3. Thereafter, the entire vascular closure device 10 is removed from the vessel puncture 82 and tissue tract 88. The bioadhesive plug 5 and the secondary bioadhesive plug 1 seal closed the vessel puncture 82 and tissue tract 88.

In other embodiments, a detachable sealing tip may be carried at the distal end 68 of the inner tube 62 and detached or disposed within the tract 3 upon removal of the vascular closure device 10. Example detachable sealing tips are disclosed in U.S. Patent Application No. 61/590,000, filed on 24 Jan. 2012, and entitled "Balloon Location Device Manifold for Vascular Closure Device and Methods," which is incorporated by reference above.

The bioadhesive materials discussed herein may comprise a single component, or may comprise multiple sealant components that are mixed together. The multiple sealant components may further react together to form a crosslinked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include proteinaceous compositions such as albumin, collagen and polylysine. Other examples include carbohydrate compositions such polyhyaluronic acid. The sealant components may also contain reactive functional groups to promote chemical crosslinking. The sealant components may be cross-linked by any known method including, for example, condensation reactions, Michael addition, and free radical. Functional groups used for cross-linking may include, for example, thiols, acrylates, amines, succinimydyls and aldehydes, to name a few.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A bioadhesive delivery catheter, comprising:
    a manifold comprising:
        a delivery device passage;
        an injection port;
    a tube insertable into the delivery device passage and comprising:
        first and second lumens positioned side-by-side, the first and second lumens being separated from each other by a separation plane, the separation plane being positioned between the first and second lumens without intersecting the first lumen or the second lumen, the first lumen having a first lumen proximal end, the second lumen having a second lumen proximal end, the proximal end of the first lumen positioned proximal of the proximal end of the second lumen within the delivery device passage, the second lumen arranged in flow communication with the injection port;
    a mixing member positioned between a proximal inlet of the injection port and the second lumen.

2. The bioadhesive delivery catheter of claim 1, wherein a proximal end of the tube includes a taper.

3. The bioadhesive delivery catheter of claim 1, wherein the tube has a reduced profile at a proximal end at a location proximal of the second lumen.

4. The bioadhesive delivery catheter of claim 1, wherein the mixing member comprises a mixing chamber defined within the delivery device passage adjacent to the tube.

5. The bioadhesive delivery catheter of claim 1, wherein the mixing member comprises a mixing insert positioned within the injection port.

6. The bioadhesive delivery catheter of claim 1, wherein the mixing member comprises at least first and second mixing inserts positioned in a passage defined in the manifold between the injection port and the delivery device passage.

7. The bioadhesive delivery catheter of claim 1, wherein the manifold includes a bioadhesive passage that extends from the injection port to the delivery device passage, the mixing member being positioned in the bioadhesive passage.

8. The bioadhesive delivery catheter of claim 1, wherein the delivery device passage includes proximal and distal passage portions, the proximal passage portion having a smaller cross-sectional shape than the distal passage portion.

9. The bioadhesive delivery catheter of claim 8, wherein the injection port defines a bioadhesive passage that intersects with the distal passage portion.

10. A method of delivering a bioadhesive material, comprising:
    providing a delivery device, a manifold and a tube, the manifold including a delivery device passage and an injection port, the tube comprising first and second lumens positioned side-by-side, the first and second lumens being separated from each other by a separation plane, the separation plane being positioned between the first and second lumens without intersecting the first lumen or the second lumen, the first lumen having a proximal end positioned proximal of a second lumen proximal end, the tube being inserted into the delivery device passage with the second lumen in flow communication with the injection port;
    extending the delivery device through the first lumen and into a vessel puncture to locate the vessel puncture;
    delivering the bioadhesive material through the injection port and the second lumen to the vessel puncture to seal closed the vessel puncture.

11. The method of claim 10, further comprising mixing the bioadhesive material while delivering the bioadhesive material through the manifold.

12. The method of claim 10, wherein the tube comprises a reduced profile at a proximal end of the tube.

13. The method of claim 10, wherein the manifold includes a mixing chamber positioned proximal of a proximal opening into the second lumen, the method including mixing the bioadhesive material in the mixing chamber during delivery of the bioadhesive material into the second lumen.

14. The method of claim 10, further comprising a mixing member positioned in the injection port, the method including mixing the bioadhesive material with the mixing member during delivery of the bioadhesive material into the second lumen.

15. A method of forming a bioadhesive delivery catheter, comprising:
    forming a manifold having a delivery device passage and an injection port;
    forming a tube having first and second lumens, the first lumen having a first lumen proximal end positioned further proximally than a second lumen proximal end, the first and second lumens being separated from each other by a separation plane, the separation plane being positioned between the first and second lumens without intersecting the first lumen or the second lumen;
    inserting the proximal ends of the first and second lumens of the tube into the delivery device passage to provide flow communication between the second lumen and the injection port;
    positioning a sealant mixing member between an inlet to the injection port and an opening into the second lumen.

16. The method of claim 15, wherein the sealant mixing member comprises a protrusion that creates turbulence in a flow of bioadhesive material delivered into the injection port.

17. The method of claim 15, wherein the sealant mixing member comprises a mixing chamber that is in fluid communication with the delivery device passage.

18. The method of claim 15, wherein the delivery device passage includes proximal and distal passage portions having different cross-sectional sizes, the tube having a reduced cross-section proximal end portion sized for insertion into the proximal passage portion.

19. The method of claim 15, further comprising forming a taper in a proximal end portion of the tube, the taper overlapping with a proximal opening into the second lumen of the tube.

20. The method of claim 15, further comprising bonding the tube to the manifold within the delivery device passage.

* * * * *